United States Patent [19]
Jones

[11] Patent Number: 6,059,100
[45] Date of Patent: May 9, 2000

[54] FEMININE HYGIENE PRODUCT DISPOSAL SYSTEM

[76] Inventor: Edith M. Jones, 11473 Newgate La., Cincinnati, Ohio 45240

[21] Appl. No.: 09/349,821

[22] Filed: Jul. 8, 1999

[51] Int. Cl.⁷ .................................................. B65D 77/04
[52] U.S. Cl. ........................... 206/210; 206/581; 206/440
[58] Field of Search .................................. 206/205, 209, 206/210, 581, 229, 233, 438, 440, 494, 812

[56] References Cited

U.S. PATENT DOCUMENTS

| | | | |
|---|---|---|---|
| 4,881,278 | 11/1989 | Farah | 206/209 X |
| 5,261,531 | 11/1993 | Nieves | 206/440 X |
| 5,484,636 | 1/1996 | Berg, Jr. et al. | 206/440 X |

*Primary Examiner*—Jacob K. Ackun

[57] ABSTRACT

A feminine hygiene product disposal system for providing a sanitary plurality of separable deodorizing disposal containers. The feminine hygiene product disposal system includes a main container having a sealable top, the main container being for holding a plurality of separable disposal containers coupled to each other in series. Each disposal container includes an interior, a sealable opening, gripping portions extending from the opening, and a deodorant pad positioned within the interior of the disposal container.

9 Claims, 2 Drawing Sheets

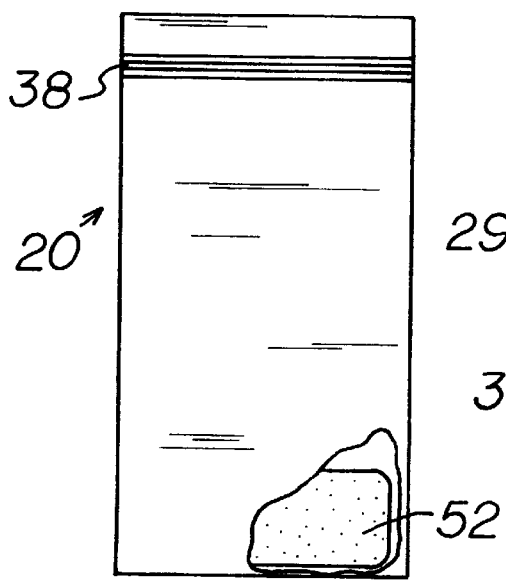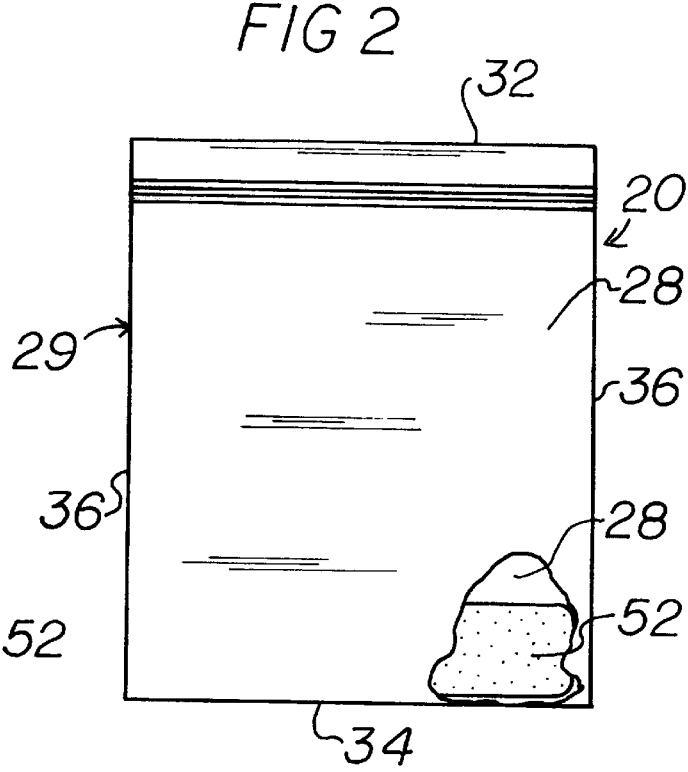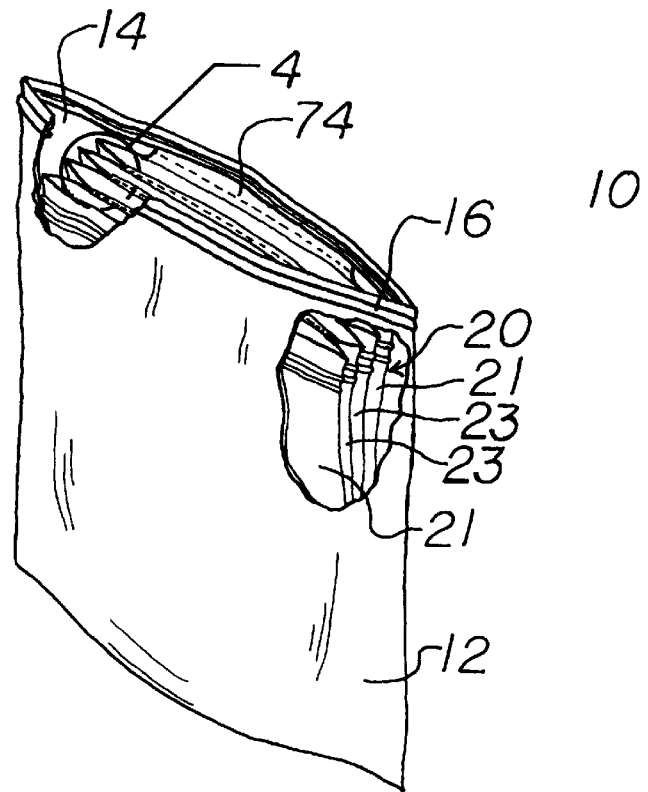

FEMININE HYGIENE PRODUCT DISPOSAL SYSTEM

BACKGROUND OF THE INVENTION

1. Field of the Invention

The present invention relates to feminine hygiene disposal products and more particularly pertains to a new feminine hygiene product disposal system for providing a sanitary plurality of separable deodorizing disposal containers.

2. Description of the Prior Art

The use of feminine hygiene disposal products is known in the prior art. More specifically, feminine hygiene disposal products heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,702,379; U.S. Pat. No. 5,690,625; U.S. Pat. No. 5,149,202; U.S. Pat. No. 5,803,256; U.S. Pat. No. 5,108,195; U.S. Pat. No. 4,349,104; U.S. Pat. No. 3,556,187; U.S. Pat. No. 5,240,484; U.S. Pat. No. 4,989,994; U.S. Pat. No. 5,358,499; U.S. Pat. No. 4,857,066; U.S. Pat. No. 675,415; U.S. Pat. No. 3,456,867; U.S. Pat. No. 5,193,684; Foreign Patent No. WO 94/08634; and Foreign Patent No. WO 96/10356.

While these devices fulfill their respective, particular objectives and requirements, the aforementioned patents do not disclose a new feminine hygiene product disposal system. The inventive device includes a main container having a sealable top, the main container being for holding a plurality of separable disposal containers coupled to each other in series. Each disposal container includes an interior, a sealable opening, gripping portions extending from the opening, and a deodorant pad positioned within the interior of the disposal container.

In these respects, the feminine hygiene product disposal system according to the present invention substantially departs from the conventional concepts and designs of the prior art, and in so doing provides an apparatus primarily developed for the purpose of providing a sanitary plurality of separable deodorizing disposal containers.

SUMMARY OF THE INVENTION

In view of the foregoing disadvantages inherent in the known types of feminine hygiene disposal products now present in the prior art, the present invention provides a new feminine hygiene product disposal system construction wherein the same can be utilized for providing a sanitary plurality of separable deodorizing disposal containers.

The general purpose of the present invention, which will be described subsequently in greater detail, is to provide a new feminine hygiene product disposal system apparatus and method which has many of the advantages of the feminine hygiene disposal products mentioned heretofore and many novel features that result in a new feminine hygiene product disposal system which is not anticipated, rendered obvious, suggested, or even implied by any of the prior art feminine hygiene disposal products, either alone or in any combination thereof.

To attain this, the present invention generally comprises a main container having a sealable top, the main container being for holding a plurality of separable disposal containers coupled to each other in series. Each disposal container includes an interior, a sealable opening, gripping portions extending from the opening, and a deodorant pad positioned within the interior of the disposal container.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new feminine hygiene product disposal system apparatus and method which has many of the advantages of the feminine hygiene disposal products mentioned heretofore and many novel features that result in a new feminine hygiene product disposal system which is not anticipated, rendered obvious, suggested, or even implied by any of the prior art feminine hygiene disposal products, either alone or in any combination thereof.

It is another object of the present invention to provide a new feminine hygiene product disposal system which may be easily and efficiently manufactured and marketed.

It is a further object of the present invention to provide a new feminine hygiene product disposal system which is of a durable and reliable construction.

An even further object of the present invention is to provide a new feminine hygiene product disposal system which is susceptible of a low cost of manufacture with regard to both materials and labor, and which accordingly is then susceptible of low prices of sale to the consuming public, thereby making such feminine hygiene product disposal system economically available to the buying public.

Still yet another object of the present invention is to provide a new feminine hygiene product disposal system which provides in the apparatuses and methods of the prior art some of the advantages thereof, while simultaneously overcoming some of the disadvantages normally associated therewith.

Still another object of the present invention is to provide a new feminine hygiene product disposal system for providing a sanitary plurality of separable deodorizing disposal containers.

Yet another object of the present invention is to provide a new feminine hygiene product disposal system which includes a main container having a sealable top, the main container being for holding a plurality of separable disposal containers coupled to each other in series. Each disposal container includes an interior, a sealable opening, gripping portions extending from the opening, and a deodorant pad positioned within the interior of the disposal container.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of a new feminine hygiene product disposal system according to the present invention.

FIG. 2 is a front view of an embodiment of the disposal containers of the present invention.

FIG. 3 is a front view of an embodiment of the disposal containers of the present invention.

DESCRIPTION OF THE PREFERRED EMBODIMENT

Figure 4:
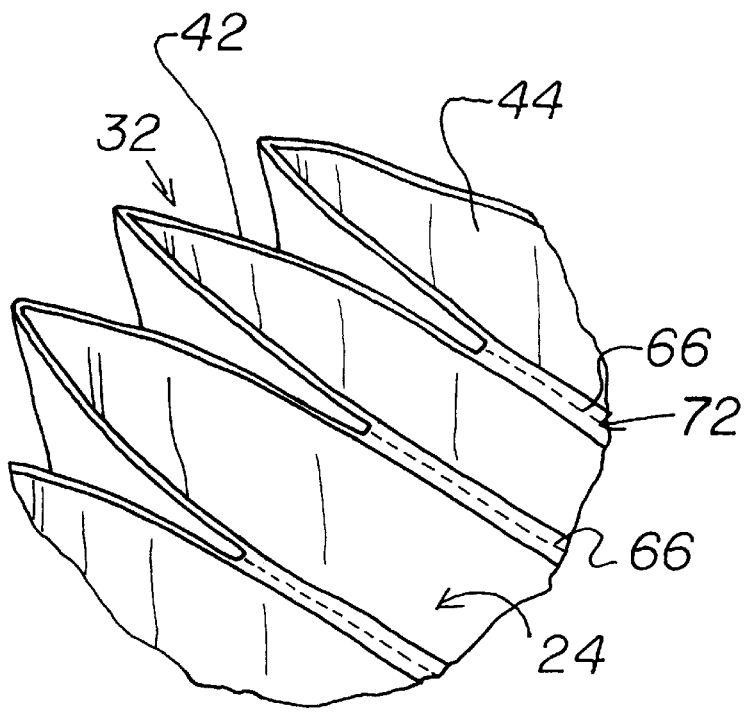
FIG. 4 is an enlarged view of an embodiment of the present invention indicated by circle 4 of FIG. 1.
Figure 5:
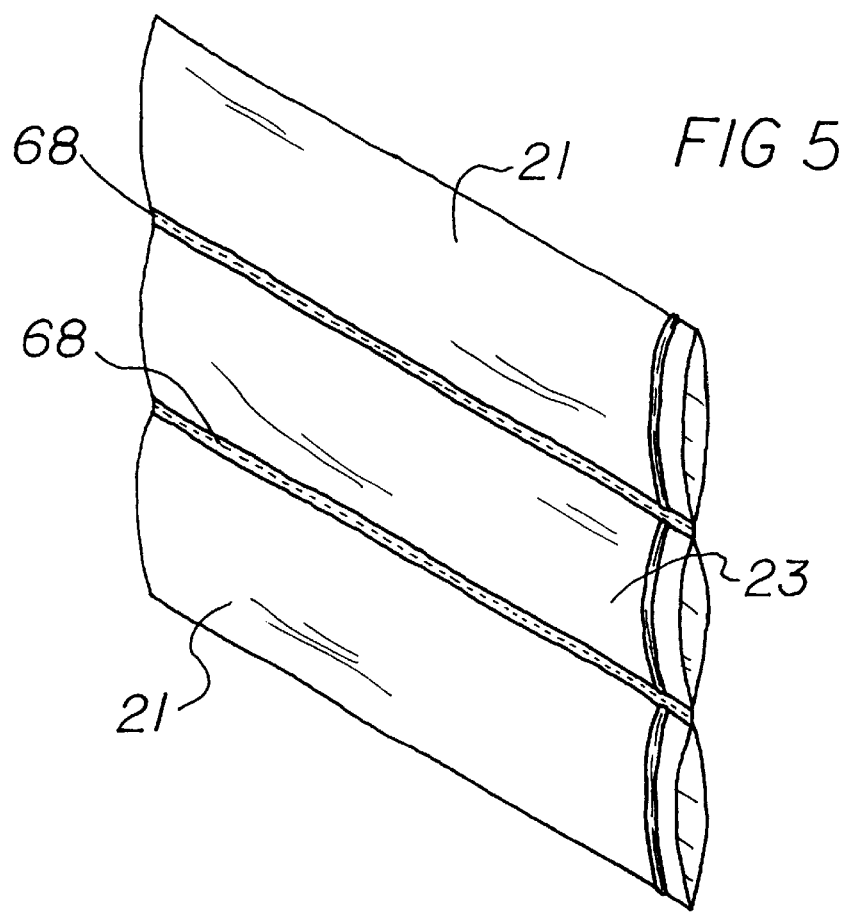
FIG. 5 is a perspective view of an embodiment of the connected disposal containers of the present invention.

With reference now to the drawings, and in particular to FIGS. 1 through 5 thereof, a new feminine hygiene product disposal system embodying the principles and concepts of the present invention and generally designated by the reference numeral 10 will be described.

As best illustrated in FIGS. 1 through 5, the feminine hygiene product disposal system 10 generally comprises a main container 12 having an interior 14 and a sealable top 16. The system 10 further includes a plurality of disposal containers 20. Each of the disposal containers is separably coupled to an adjacent one of the disposal containers.

Each of the disposal containers includes an interior chamber 22 designed for holding a used feminine hygiene product. Each of the disposal containers includes a sealable opening 24 for sealing the interior chamber such that the disposal container is designed to prevent environmental communication between the interior chamber of the disposal container and a surrounding environment.

Each of the plurality of disposal containers also includes a pair of panels 28 having an outer peripheral edge 29. In an embodiment, the flexible panels are constructed of a flexible air impervious material. The material is most preferably opaque to obscure viewing of the used feminine hygiene product once it has been inserted into the disposal container. Each outer peripheral edge includes a top peripheral portion 32, a bottom peripheral portion 34 and two side peripheral portions 36 extending between the top peripheral portion and the bottom peripheral portion. The bottom peripheral portions and the side peripheral portions of the panels are coupled together such that the pair of panels forms the disposal container.

The sealable opening 24 is formed by a locking track 38 extending between the side peripheral portions proximate the top peripheral portions of the panels. The locking track is positioned such that the sealable opening is substantially parallel to the top peripheral portions of the panels.

Each top peripheral portions includes a top edge 42. The top edge is offset from the locking track to form a gripping portion 44 for facilitating opening of the disposal container.

Each disposal container includes an associated deodorant pad 52 positioned within the interior chamber of the disposal container. In an embodiment, each deodorant pad is impregnated with an anti-bacterial substance. In an embodiment, each pad may include an odor absorbing substance such as charcoal. Each deodorant pad is generally elongate and rectangular in shape and is positioned proximate the bottom peripheral portions of the panels for providing additional stiffness and weight to the bottom of each disposal container. The stiffness across the disposal container and the added weight to the bottom is designed to facilitate insertion of the otherwise flexible disposal containers into the main container.

The plurality of disposal containers including a pair of outer disposal containers 21 and at least one interior disposal container 23 positioned between the outer disposal containers. In an embodiment each side peripheral portion of each interior disposal container is conjoined to an associated side peripheral portion of an adjacent one of the plurality of disposal containers. A side score line 68 extends between the conjoined side peripheral portions for facilitating separation of each disposal container from an adjacent disposal container.

In an embodiment, each top edge of each of the interior disposal containers includes a central portion 72 conjoined to the top edge of an adjacent one of the disposal containers. The central portion includes a top score line 66 for facilitating separation of each disposal container from an adjacent disposal container. In an embodiment, one of the top edges of one of the two outer disposal containers is conjoined to the sealable top of said main container. A main score line 74 extends between the outer disposal container and the sealable top for facilitating separation of the one outer disposal container from the main container.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A feminine hygiene product disposal system, comprising:
   a main container having an interior and a sealable top;
   a plurality of disposal containers, each of said disposal containers being separably coupled to an adjacent one of said disposal containers;
   each of said disposal containers having an interior chamber adapted for holding a used feminine hygiene product therein;
   each of said disposal containers having a sealable opening for sealing said interior chamber such that said interior chamber is adapted to prevent environmental communication between said interior chamber of said disposal container and a surrounding environment.

2. The feminine hygiene product disposal system of claim 1, further comprising:
   each of said plurality of disposal containers having a pair of panels having an outer peripheral edge;
   each said outer peripheral edge having a top peripheral portion, a bottom peripheral portion and two side peripheral portions extending between the top peripheral portion and the bottom peripheral portion;
   said bottom peripheral portions and said side peripheral portions being coupled together such that said pair of panels forms said disposal container;
   said sealable opening being formed by a locking track extending between said side peripheral portions proximate said top peripheral portions such that said sealable opening is substantially parallel to said top peripheral portions.

3. The feminine hygiene product disposal system of claim 2, further comprising:
   each said top peripheral portions having a top edge, said top edge being offset from said locking track to form a gripping portion for facilitating opening of said disposal container.

4. The feminine hygiene product disposal system of claim 1, further comprising:
   a plurality of deodorant pads, each disposal container having an associated deodorant pad positioned within said interior chamber.

5. The feminine hygiene product disposal system of claim 2, further comprising:
   said plurality of disposal containers including a pair of outer disposal containers and at least one interior disposal container positioned between said outer disposal containers;
   each top edge of each of said interior disposal containers having a central portion conjoined to the top edge of an adjacent one of said plurality of disposal containers; and
   said central portion having a top score line for facilitating separation of one said disposal container from an adjacent disposal container.

6. The feminine hygiene product disposal system of claim 2, further comprising:
   said plurality of disposal containers including a pair of outer disposal containers and at least one interior disposal container positioned between said outer disposal containers;
   each side peripheral portion of each said interior disposal container being conjoined to an associated side peripheral portion of an adjacent one of said plurality of disposal containers; and
   a side score line extending between said conjoined side peripheral portions for facilitating separation of one said disposal container from an adjacent disposal container.

7. The feminine hygiene product disposal system of claim 4, wherein each said deodorant pad is impregnated with an anti-bacterial substance.

8. A feminine hygiene product disposal system, comprising:
   a main container having an interior and a sealable top;
   a plurality of disposal containers, each of said disposal containers being separably coupled to an adjacent one of said disposal containers;
   each of said disposal containers having an interior chamber adapted for holding a used feminine hygiene product therein;
   each of said disposal containers having a sealable opening for sealing said interior chamber such that said interior chamber is adapted to prevent environmental communication between said interior chamber of said disposal container and a surrounding environment;
   each of said plurality of disposal containers having a pair of panels having an outer peripheral edge;
   each said outer peripheral edge having a top peripheral portion, a bottom peripheral portion and two side peripheral portions extending between the top peripheral portion and the bottom peripheral portion;
   said bottom peripheral portions and said side peripheral portions being coupled together such that said pair of panels forms said disposal container;
   said sealable opening being formed by a locking track extending between said side peripheral portions proximate said top peripheral portions such that said sealable opening is substantially parallel to said top peripheral portions;
   each said top peripheral portions having a top edge, said top edge being offset from said locking track to form a gripping portion for facilitating opening of said disposal container;
   a plurality of deodorant pads, each disposal container having an associated deodorant pad positioned within said interior chamber;
   said plurality of disposal containers including a pair of outer disposal containers and at least one interior disposal container positioned between said outer disposal containers;
   each side peripheral portion of each said interior disposal container being conjoined to an associated side peripheral portion of an adjacent one of said plurality of disposal containers; and
   a side score line extending between said conjoined side peripheral portions for facilitating separation of one said disposal container from an adjacent disposal container;
   wherein each said deodorant pad is impregnated with an anti-bacterial substance.

9. A feminine hygiene product disposal system, comprising:
   a main container having an interior and a sealable top;
   a plurality of disposal containers, each of said disposal containers being separably coupled to an adjacent one of said disposal containers;
   each of said disposal containers having an interior chamber adapted for holding a used feminine hygiene product therein;

each of said disposal containers having a sealable opening for sealing said interior chamber such that said interior chamber is adapted to prevent environmental communication between said interior chamber of said disposal container and a surrounding environment;

each of said plurality of disposal containers having a pair of panels having an outer peripheral edge;

each said outer peripheral edge having a top peripheral portion, a bottom peripheral portion and two side peripheral portions extending between the top peripheral portion and the bottom peripheral portion;

said bottom peripheral portions and said side peripheral portions being coupled together such that said pair of panels forms said disposal container;

said sealable opening being formed by a locking track extending between said side peripheral portions proximate said top peripheral portions such that said sealable opening is substantially parallel to said top peripheral portions;

each said top peripheral portions having a top edge, said top edge being offset from said locking track to form a gripping portion for facilitating opening of said disposal container;

a plurality of deodorant pads, each disposal container having an associated deodorant pad positioned within said interior chamber;

said plurality of disposal containers including a pair of outer disposal containers and at least one interior disposal container positioned between said outer disposal containers;

each top edge of each of said interior disposal containers having a central portion conjoined to the top edge of an adjacent one of said plurality of disposal containers;

said central portion having a top score line for facilitating separation of one said disposal container from an adjacent disposal container;

wherein each said deodorant pad is impregnated with an anti-bacterial substance;

one of said top edges of one of said outer disposal containers being conjoined to said sealable top of said main container; and a main score line extending between said one outer disposal container and said sealable top for facilitating separation of said one outer disposal container from said main container.

\* \* \* \* \*